(12) United States Patent
Sauer et al.

(10) Patent No.: US 8,007,471 B2
(45) Date of Patent: Aug. 30, 2011

(54) MEDICAL INSTRUMENT WITH LATERALLY DISPLACEABLE SEAL

(75) Inventors: Michael Sauer, Tuttlingen (DE); Elmar Teichtmann, Eppingen (DE)

(73) Assignee: Karl Storz GmbH & Co. KG (DE)

( * ) Notice: Subject to any disclaimer, the term of this patent is extended or adjusted under 35 U.S.C. 154(b) by 91 days.

(21) Appl. No.: 12/507,486

(22) Filed: Jul. 22, 2009

(65) Prior Publication Data

US 2010/0022957 A1    Jan. 28, 2010

(30) Foreign Application Priority Data

Jul. 23, 2008  (DE) .................. 10 2008 035 311

(51) Int. Cl.
*A61M 5/178* (2006.01)

(52) U.S. Cl. .................................... 604/164.03

(58) Field of Classification Search .......... 604/164.01, 604/164.03
See application file for complete search history.

(56) References Cited

U.S. PATENT DOCUMENTS

| | | | |
|---|---|---|---|
| 5,342,315 A | | 8/1994 | Rowe et al. |
| 5,492,304 A | * | 2/1996 | Smith et al. ............ 251/149.1 |
| 5,603,702 A | * | 2/1997 | Smith et al. ............ 604/256 |
| 7,413,559 B2 | * | 8/2008 | Stubbs et al. .......... 604/167.01 |
| 7,842,013 B2 | * | 11/2010 | Haberland et al. ...... 604/167.03 |
| 7,842,014 B2 | * | 11/2010 | Schweitzer et al. ..... 604/167.06 |
| 2005/0216028 A1 | * | 9/2005 | Hart et al. ................ 606/108 |
| 2007/0282371 A1 | * | 12/2007 | Lee et al. ................. 606/205 |
| 2008/0046000 A1 | * | 2/2008 | Lee et al. ................. 606/205 |
| 2008/0065116 A1 | * | 3/2008 | Lee et al. ................. 606/142 |
| 2008/0255420 A1 | * | 10/2008 | Lee et al. ................. 600/137 |
| 2009/0069842 A1 | * | 3/2009 | Lee et al. ................. 606/205 |
| 2009/0171147 A1 | * | 7/2009 | Lee et al. ................. 600/104 |
| 2010/0022957 A1 | * | 1/2010 | Sauer et al. ............ 604/164.03 |
| 2010/0049145 A1 | * | 2/2010 | Teichtmann et al. ..... 604/256 |

FOREIGN PATENT DOCUMENTS

| | | |
|---|---|---|
| EP | 0696459 B1 | 11/1998 |
| EP | 1582158 A1 | 10/2005 |
| WO | 9952577 A1 | 10/1999 |

OTHER PUBLICATIONS

European Search Report; Application No. EP 09 16 6104; Apr. 23, 2010; 5 pages.

\* cited by examiner

*Primary Examiner* — Nicholas D Lucchesi
*Assistant Examiner* — Diva Ranade
(74) *Attorney, Agent, or Firm* — St. Onge Steward Johnston Reens LLC

(57) ABSTRACT

A medical instrument has a cannula, a seal disposed in said cannula, said seal has an opening for guiding a shaft of another instrument through said seal in a sealed manner. An expansion device serves for expanding said opening in said seal. Said expansion device has an expansion cone comprising a plurality of slats mounted pivotably on an annular body at a first end, a second end of said slots opposite to said first end being connected to said seal in an area of said opening. A flexible casing structure is provided accommodating said seal and said expansion device.

14 Claims, 8 Drawing Sheets

US 8,007,471 B2

MEDICAL INSTRUMENT WITH LATERALLY DISPLACEABLE SEAL

BACKGROUND OF THE INVENTION

The present invention relates to a medical instrument, with a cannula through which shafts of other instruments having different shaft diameters can be guided, with a seal comprising an opening with a variable opening cross section through which the shafts having different shaft diameters can be guided sealingly, with an expansion device for expanding the opening of the seal, which expansion device has an expansion cone with a plurality of slats that are mounted pivotably on an annular body and form an expansion body that narrows from the proximal end to the distal end and that is connected at the distal end to the seal in the area of the opening.

A medical instrument of this kind is known from EP 0 696 459 B1.

Said medical instrument is a trocar that is used in minimally invasive surgery. The trocar is introduced through a small opening, which is formed by a small incision in the skin for example, through the abdominal wall into the abdominal cavity of the patient by means of a trocar mandrel. After removal of the trocar mandrel, shafts of other instruments used for the surgical intervention are then passed through this trocar. These instruments include, for example, gripping tools, coagulation instruments, endoscopes and the like. These have shafts of different diameters.

Since minimally invasive interventions of this kind are often performed during insufflation of the internal cavity in which the operation takes place, all the intervention points must be gas-tight.

In the aforementioned EP 0 696 459 B1, this purpose is served by an elastic conical seal that is arranged in the trocar and that narrows from the proximal end to the distal end. To permit a uniform widening of the seal when an instrument of a diameter larger than the opening in the seal is inserted into the trocar, an expansion cone is arranged in the proximal direction from this seal. An instrument inserted into the expansion cone expands the latter radially, which in turn widens the opening in the seal. The expansion cone also prevents damage to the seal during insertion of sharp-edged instruments.

Upon insertion of an instrument having a shaft diameter corresponding approximately to that of the cannula of the trocar, the instrument expands the opening to the maximum extent, and the whole circumference of the shaft comes uniformly into contact with the seal. In this way, the trocar system is sealed off at the proximal end. Whenever a shaft of an instrument is inserted into the opening of the seal, said shafts having a diameter of at least the opening or larger.

Insertion of an instrument having a slender shaft which is only a little bit larger than the original size of the opening can become offset from the central passage through the opening of the seal. Moreover, particularly in the case of narrower flexible shafts, the shaft may tilt in the trocar.

Both of these situations have the effect that the seal does not come uniformly into contact with the shaft about the whole circumference of the latter. This results in undesirable leaks. These lead to an escape of the gas, which has been admitted for the operation, and, consequently, to a loss of the insufflation.

The insertion of instruments with narrow shafts can therefore be problematic and may cause difficulties.

It is therefore an object of the present invention to develop a medical instrument of this kind in such a way that a lateral offset of an inserted shaft cannot lead to a loss of leaktightness of the trocar.

SUMMARY OF THE INVENTION

This object is achieved according to the invention by a medical instrument having a cannula, a seal disposed in said cannula, said seal has an opening for guiding a shaft of another instrument through said seal and said cannula in a sealed manner, an expansion device for expanding said opening in said seal for guiding shafts of said other instruments of greater diameter in a sealed manner through said expanded opening, said expansion device having an expansion cone comprising a plurality of slats mounted pivotably on an annular body at a first end, a second end of said slats opposite to said first end, being connected to said seal in an area of said opening, and an flexible casing structure accommodating said and said expansion device.

The assembly composed of the expansion cone and the seal, made of elastic material, forms a structure that is relatively unstable in the lateral direction. This is particularly so in the configuration in which the expansion cone and the seal extend diametrally away from each other starting from their point of connection to each other. An instrument inserted with a lateral offset or obliquely into the expansion cone would cause a lateral shift or lateral displacement of the assembly. The casing structure surrounding the assembly of seal and expansion cone counteracts this, but provides a certain degree of flexibility.

When there is a non-uniform contact between an inserted shaft and the opening of the seal, the flexible casing structure shifts the sealing system in such a way that the shaft extends centrally through the opening of the seal. In this way, the seal once again comes into uniform contact with the shaft about the whole circumference of the latter, as a result of which the desired leaktightness of the trocar system is maintained. The casing structure effects a kind of straightening or aligning of the assembly of seal and expansion cone to the rectilinear orientation.

The casing structure thus gives the assembly of expansion cone and seal, an increased stability, which is lacking particularly in the embodiment in which the seal extends in the distal direction away from the distal end of the expansion cone. Since the seal is very movable, the expansion cone is thereby also very movable and, consequently, also the inlet opening into the trocar. This makes inserting a shaft into the trocar difficult and, because of oblique positions of the seal, can also have a negative effect on the sealing properties of the sealing system. This is counteracted by the casing structure, since the latter establishes an additional connection of the proximal end of the expansion cone to the trocar and thus reduces the mobility of the sealing system to a desired degree.

If the casing structure is designed as a flexible casing tube a stabilization of the assembly of seal and expansion cone is very proper.

In another embodiment of the invention, the flexible casing tube is composed of a substantially parallel series of ring elements, wherein two adjacent ring elements are preferably connected to each other at two radially opposite sites, and, furthermore, the sites connecting a ring element to the distally adjacent ring element are in each case always offset by 90° with respect to the connecting sites to the proximally adjacent ring element.

The connecting sites between the ring elements, arranged in a circle shape and alternately offset by 90°, permit a flexibility of the casing tube in all lateral directions since, as a result of the connecting sites being arranged radially opposite one another, the connected ring elements have a tilt axis.

By means of this, they can be tilted towards one another, from the mutually parallel arrangement, at sites lying circumferentially between the connecting sites. Within the overall arrangement of the ring elements, the 90° offset from one pair to the next pair of ring elements ensures that certain tilting is possible in two mutually perpendicular directions. That is to say, the casing structure thus formed can be moved at its free proximal end in two independent directions and, therefore, in the plane defined by these directions. In addition to the good mobility, and the associated ability to compensate for an offset of a shaft in the trocar, the connecting sites offset by 90° to each other at the same time provide good axial stability since, in the event of loading, the acting forces are distributed uniformly.

A further advantage of using ring elements is that they are fairly uncomplicated structural components, which simplifies production.

In one embodiment of the invention, the connections are flexible webs.

The advantage of this embodiment is that the narrow and therefore flexible webs are arranged directly on the respective elements without multi-part hinges. In this way, the flexible casing tube thereby formed can be produced as a single workpiece, e.g. from plastic, by an injection moulding technique. Since this does away with subsequent assembling of the ring elements, production is very quick and straightforward.

In one embodiment of the invention, the connections are tilting joints.

By constructing the flexible casing tube from individual ring elements and connecting these by means of tilting joints, the length of the flexible casing tube can be varied. In the design of a sealing system, this length can therefore be adapted to the length of the expansion cone and to the length of the seal. With one type of ring element, it is therefore possible to construct casing tubes of different lengths, which means that this embodiment affords great variability.

In one embodiment of the invention, the ring elements have at the tilting joints at least one tilting-joint socket and at least one tilting-joint insert extending radially from said ring element, said ring elements have a height being higher at the sites of a tilting-joint socket than at those of a tilting-joint insert.

The site of the tilting-joint socket in the ring element must have a certain height in order to be able to receive the complete tilting-joint insert. This height is lower at the other parts of the ring element. In this way, there is an area in which the ring elements can be tilted relative to one another, since the distance between the ring elements is greater at the sites lying circumferentially between the tilting joints. In this way, the greatest possible angle of inclination is achieved, which increases the flexibility of the casing tube. As a result, the sealing system can better adapt to any offset of a shaft in the opening of the seal.

In another embodiment of the invention, the flexible casing structure widens conically from the proximal end to the distal end.

By means of this widening, the casing structure is adapted to the difference in cross section between the annular body of the expansion cone and the in most cases greater cross section of the distal end of the seal. This ensures, on the one hand, a good hold on the distal end of the seal and the trocar housing on which the latter is arranged and, on the other hand, on the expansion cone. This leads to the desired stability.

In another embodiment, the seal is designed as a pot-seal and extends in the distal direction away from the distal end of the expansion cone.

The choice of this structural arrangement has the advantage, on the one hand, that joining together the expansion cone and the seal is simple, since both components are connected to each other via easily accessible outer faces. These are the bottom of the pot seal having the opening and the expansion cone connected with its narrower end to the rim of the opening. On the other hand, the resulting arrangement of the seal facilitates the removal of tissue samples, since it in this way has a funnel-like shape that narrows from the distal end to the proximal end. If, for example, such a sample is taken hold of by a gripping tool and is then guided through the trocar sleeve in the proximal direction, it finally reaches the sealing system. There, by virtue of the gradually decreasing diameter of the seal, it is guided to the proximal narrow opening of the seal and, if appropriate, also adapted in shape. This avoids an undesirable situation in which the sample, during its removal, becomes caught because of an abrupt change in diameter.

In another embodiment of the invention, the distal end of the slats of the expansion cone is connected with a form fit to a socket at the edge of the opening in the seal.

This connection of the distal end of the slats to the opening of the seal prevents the slats from slipping during expansion of the seal. This therefore counters a possibility of the slats becoming wedged and ensures uniform expansion. Moreover, the connection has the effect that, after the removal of a shaft from the trocar, the slats move back to the starting position again together with the sealing opening, on account of the restoring force of the expanded elastic seal.

In one embodiment of the invention, the distal end of the slats of the expansion cone is adhesively bonded to the seal.

Adhesive bonding between the slats and the opening of the seal ensures a non-releasable and secure contact between the components. Undesired separation of the components is thereby avoided, such that the slats are at all times arranged on the opening of the seal. The adhesive bonding is conceivable as a single measure, but also in combination with the form-fit connection.

In another embodiment of the invention, the expansion cone is composed of eight to twelve slats, preferably ten slats.

The use of eight to twelve slats, preferably ten slats, permits uniform widening of the opening of the seal, since the number of slats used is such that the gaps arising during widening are as small as possible and, in addition, the distance between two slats in the expanded state is small. Thus, even in the expanded state, a uniform and round shape is still formed by the slats at the opening of the seal. This in particular enhances the leaktightness at the opening of the seal during and after the insertion of a shaft. Moreover, however, these slats also have sufficient stability, since they still have a sufficiently great width. They are therefore not damaged or destroyed by insertion of especially sharp-edged instruments, thereby also providing protection of the seal.

In other embodiments of the invention, the expansion cone and the flexible casing structure are made of hard plastic.

In the present case, the use of hard plastic for the expansion cone and the flexible casing structure represents a good compromise, since this provides sufficient stability, e.g. during insertion of sharp-edged instruments, but still permits simple production, for example by injection moulding.

In another embodiment of the invention, the seal is made of an elastic material.

The use of an elastic material for the seal permits suitable widening of the opening of the seal by the expansion cone during insertion of the shaft of an instrument and, at the same time, permits optimal sealing of the shaft of such an instrument, by virtue of the tight contact between elastic material and shaft. This is achieved in particular by the fact that the expanded opening of the seal is pressed against the circumference of the inserted shaft by virtue of the restoring force of the elastic material.

It will be appreciated that the aforementioned features and those still to be explained below can be used not only in the respectively cited combination but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which.

DETAILED DESCRIPTION OF PREFERRED EMBODIMENTS

A medical instrument shown in the figures is designated in its entirety by reference number 10.

Figure 1:
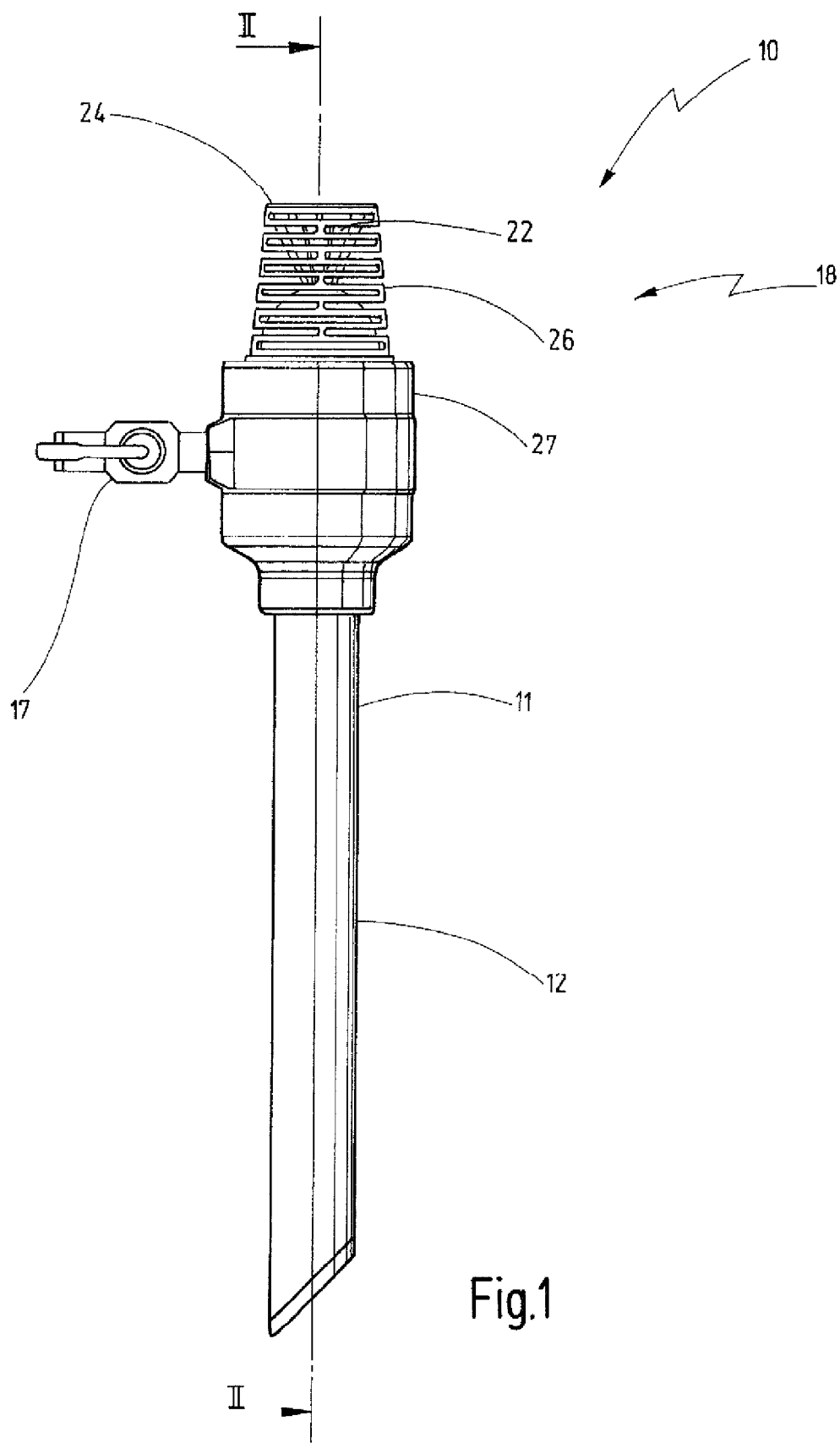
FIG. 1 shows a perspective side view of a medical instrument with a variable seal.
Figure 2:
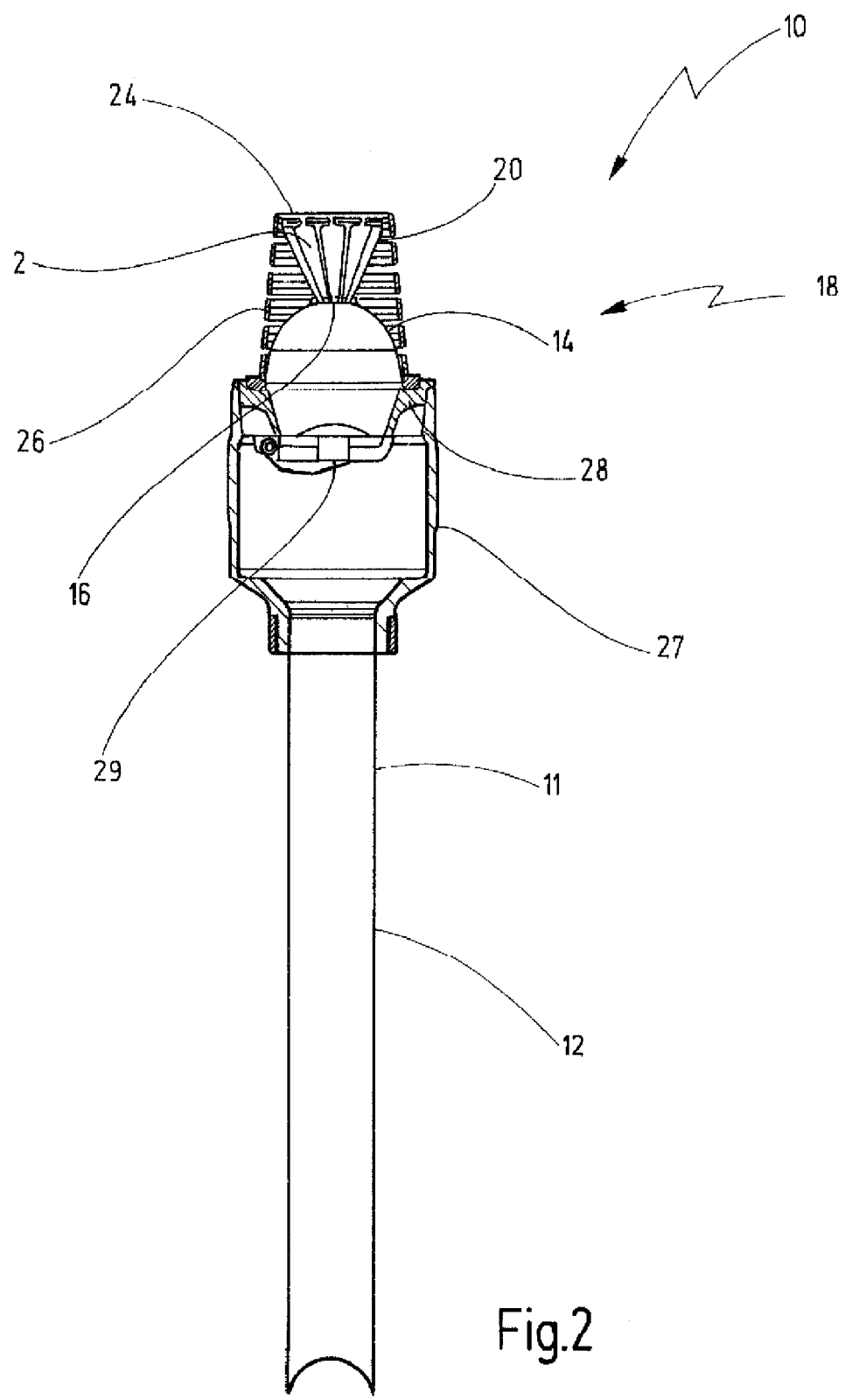
FIG. 2 shows a partial cross section along the line II-II in FIG. 1.
Figure 3:
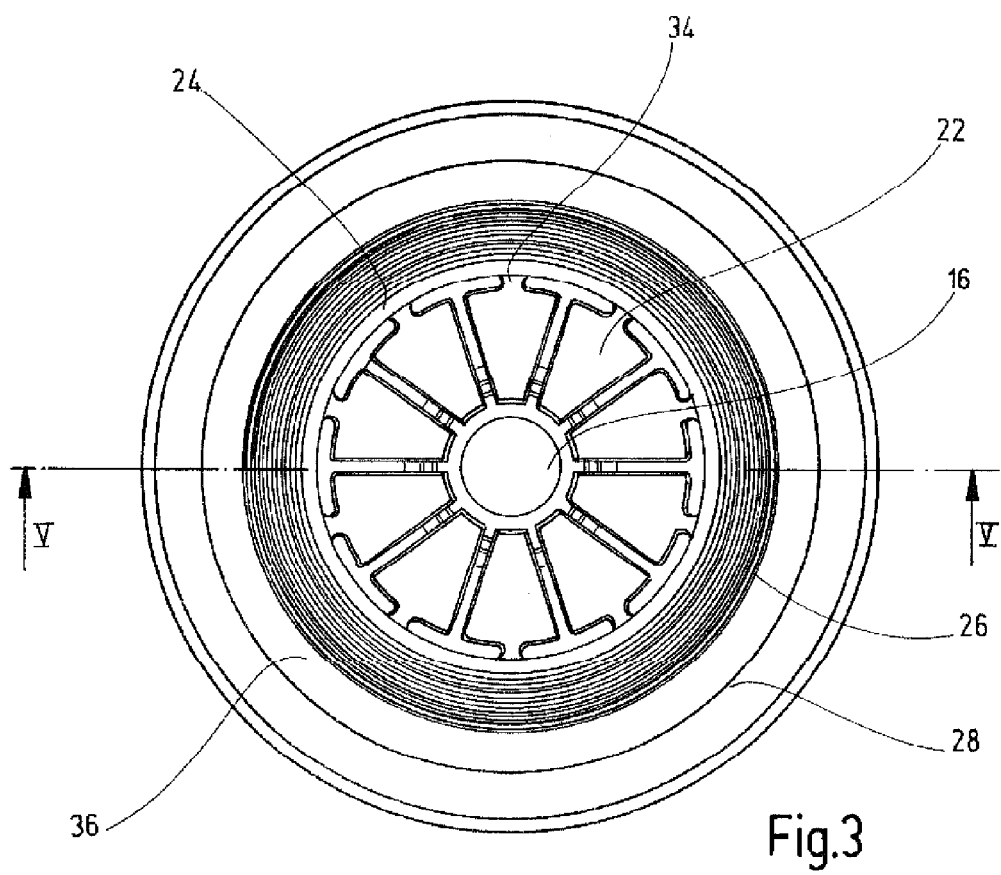
FIG. 3 shows a sealing system of the medical instrument, viewed from the proximal direction.

The medical instrument 10 shown is a trocar and has at its distal end a trocar sleeve 11, formed here by a cannula 12, at its centre a trocar housing 27 and, arranged at the proximal end of the latter, a sealing system 18. FIG. 1 also shows a valve 17, which is arranged on the trocar housing 27 and which can serve, for example, as an admission line for gases. These are used to perform insufflation of the operating site, in order thereby to obtain better access to the organs, vessels, tissues or the like, on which the operation is to be performed. In order to avoid undesired escape of the gases through the trocar in the proximal direction, a self-closing obturator 29 is arranged in the distal direction from the sealing system 18 (FIG. 2). It closes the proximal opening as soon as there is no shaft inserted into the medical instrument 10.

Figure 5:
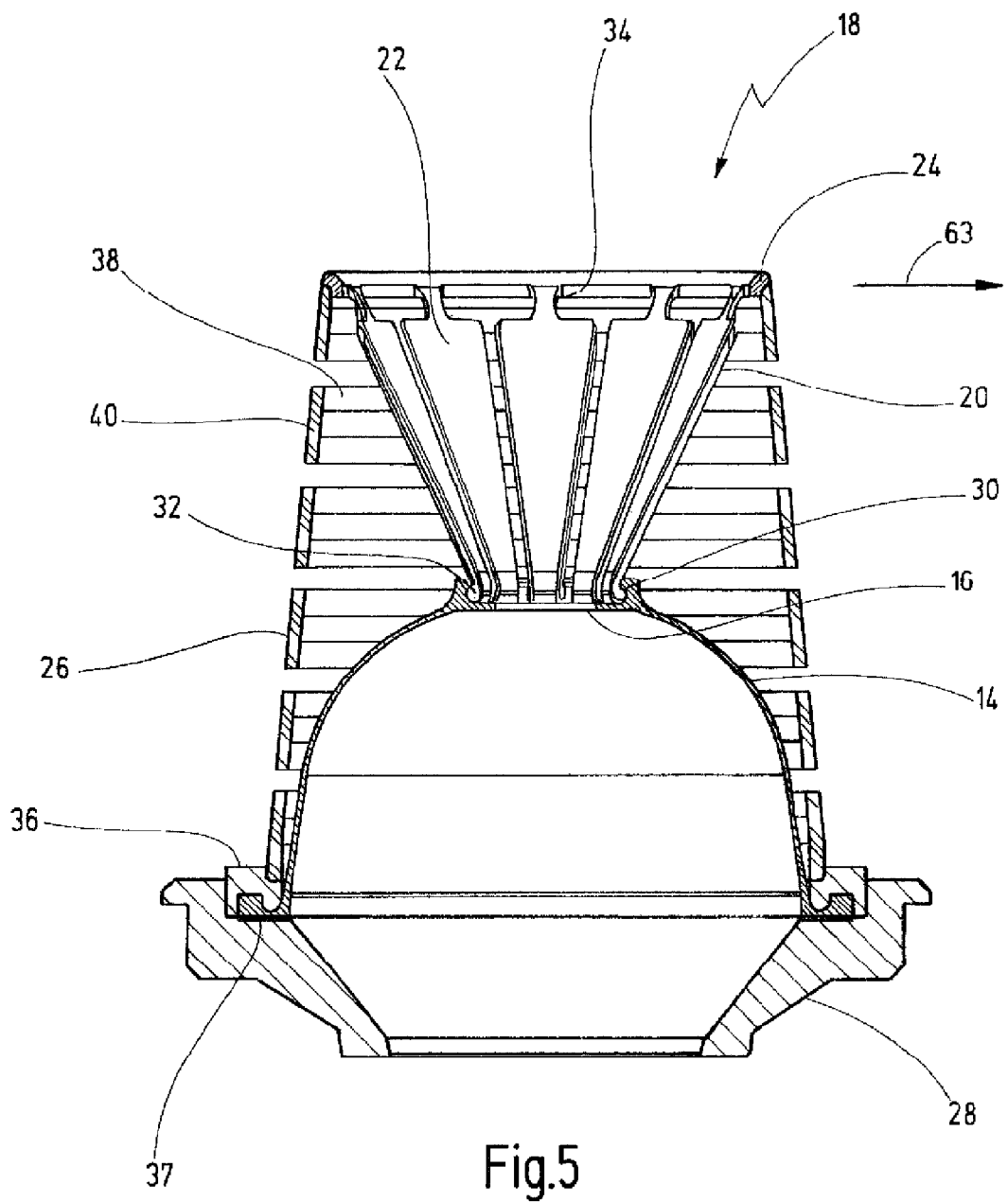
FIG. 5 shows a cross section along the line V-V in FIG. 3.
Figure 7:
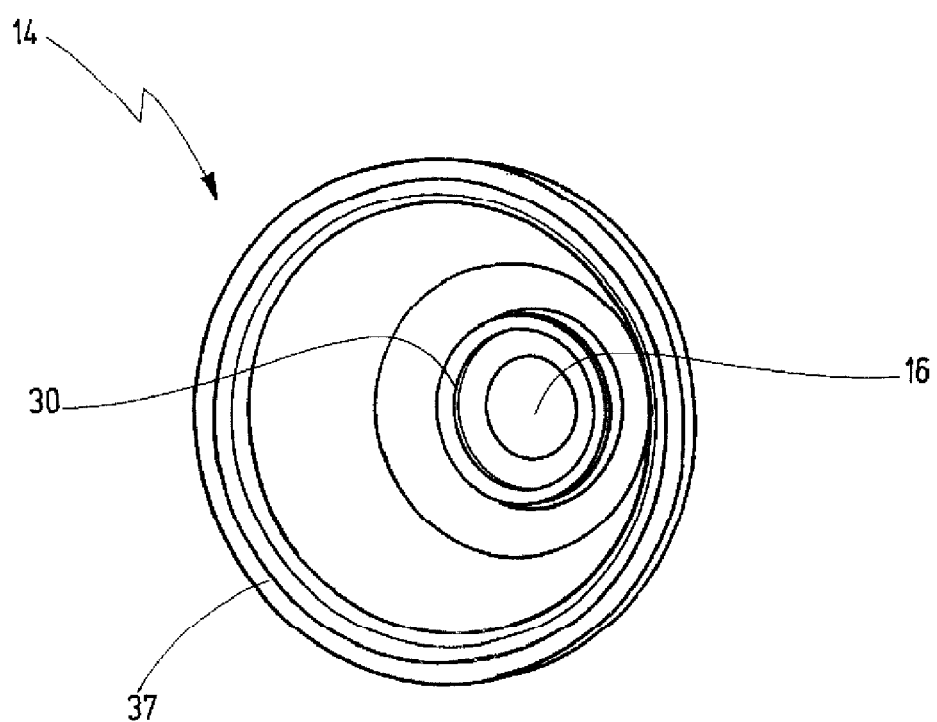
FIG. 7 shows a perspective view of a seal.

As can be seen from FIGS. 1, 2 and 5, the sealing system 18 comprises a seal 14. The seal 14 is designed as a pot-seal. The pot-seal has a peripheral edge designed as a sealing edge. An opening 16 is provided in a bottom area of the pot-seal. The sealing edge 37 of the latter is fastened by a fastening ring 36 to a seal holder 28, with which the sealing system 18 is mounted on the trocar housing 27. The seal 14 extends in the proximal direction away from the seal holder 28 and in so doing narrows. At its proximal end, the seal 14 has a socket 30 that surrounds this opening 16 (FIGS. 5 and 7). An expansion cone 20 is secured on the socket 30 and extends in the proximal direction away from the seal 14 (FIG. 5).

Figure 6:
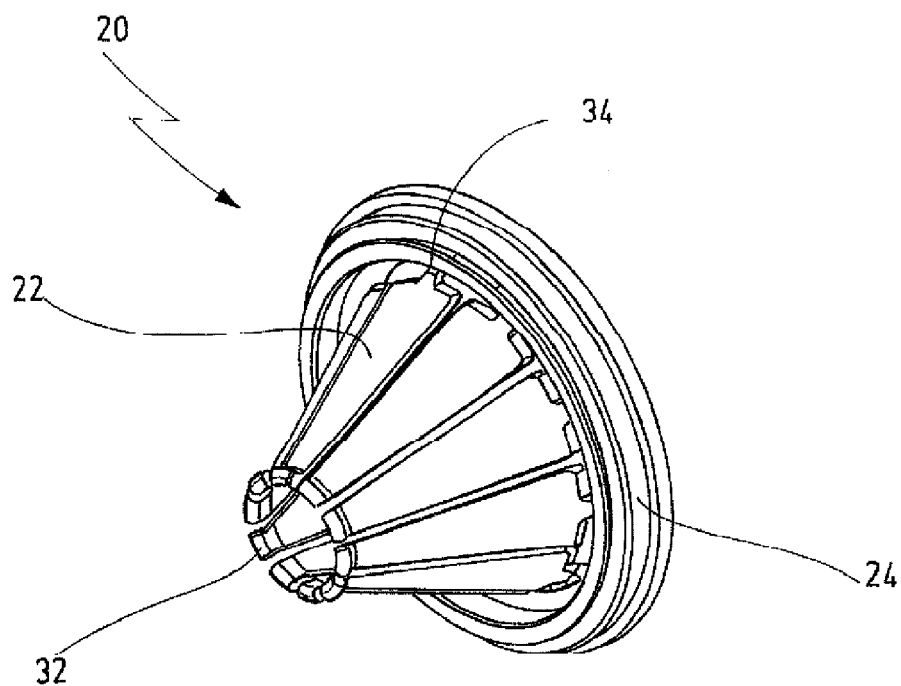
FIG. 6 shows a perspective view of an expansion cone.

As can be seen from FIGS. 5 and 6, this expansion cone 20 is composed of an annular body 24 on which first ends of slats 22, oriented in the distal direction, are mounted pivotably by means of film hinges 34 in a ring shape. At the second distal end, these slats 22 have endpieces 32 that are connected with a form fit to the socket 30 of the seal 14. The expansion cone 20 acquires its conical shape as a result of the difference in cross section between the annular body 24 and the socket 30. The slats 22 narrow from the proximal end to the distal end in such a way as to provide a uniform and almost closed inner surface of the expansion cone 20 in the unexpanded state.

The connection between the slats 22 and the seal 14, wherein the endpieces 32 are fitted in the socket 30, means that when a shaft is inserted and impacts on the slats, the slats 22 are initially forced radially outwards, as a result of which the opening 16 of the seal 14 is at the same time expanded, but without being expanded directly by the shaft.

Figure 4:
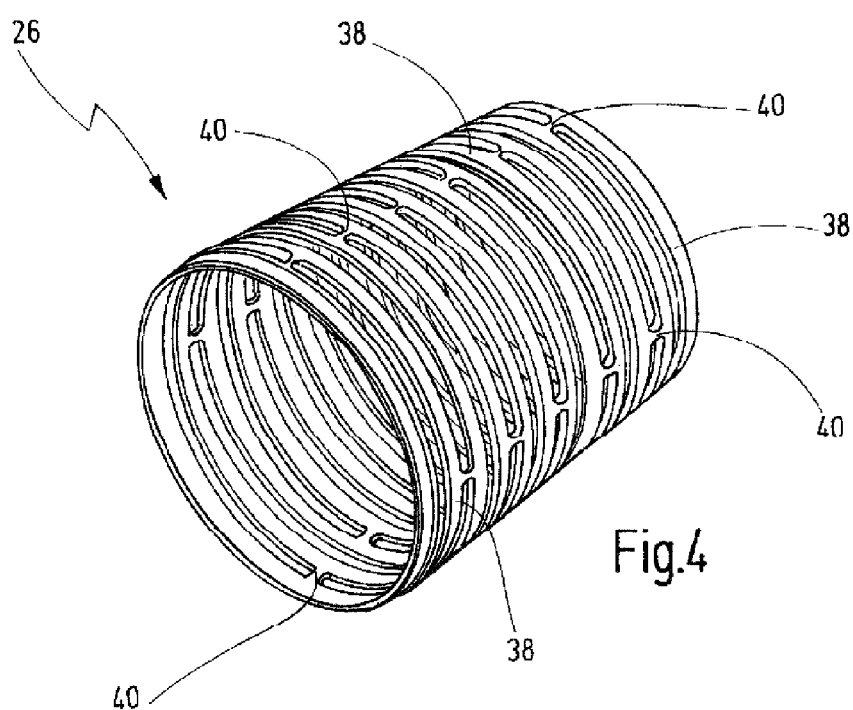
FIG. 4 shows a perspective view of a flexible casing structure of the sealing system.

The assembly composed of the seal 14 and of the expansion cone 20 is enclosed by a casing structure designed as a casing tube 26. For this purpose, this casing tube 26 is connected at the distal end to the seal holder 28 and at the proximal end to the annular body 24 (FIG. 5). The casing tube 26 is composed of individual ring elements 38, which are interconnected via webs 40 lying radially opposite each other (FIG. 4). To obtain a flexibility of the casing tube, the latter is made of a sufficiently elastic material, to ensure a flexibility of the webs 40, and the webs 40 are in each case also offset by 90° from one to the next pair of ring elements.

Figure 5A:
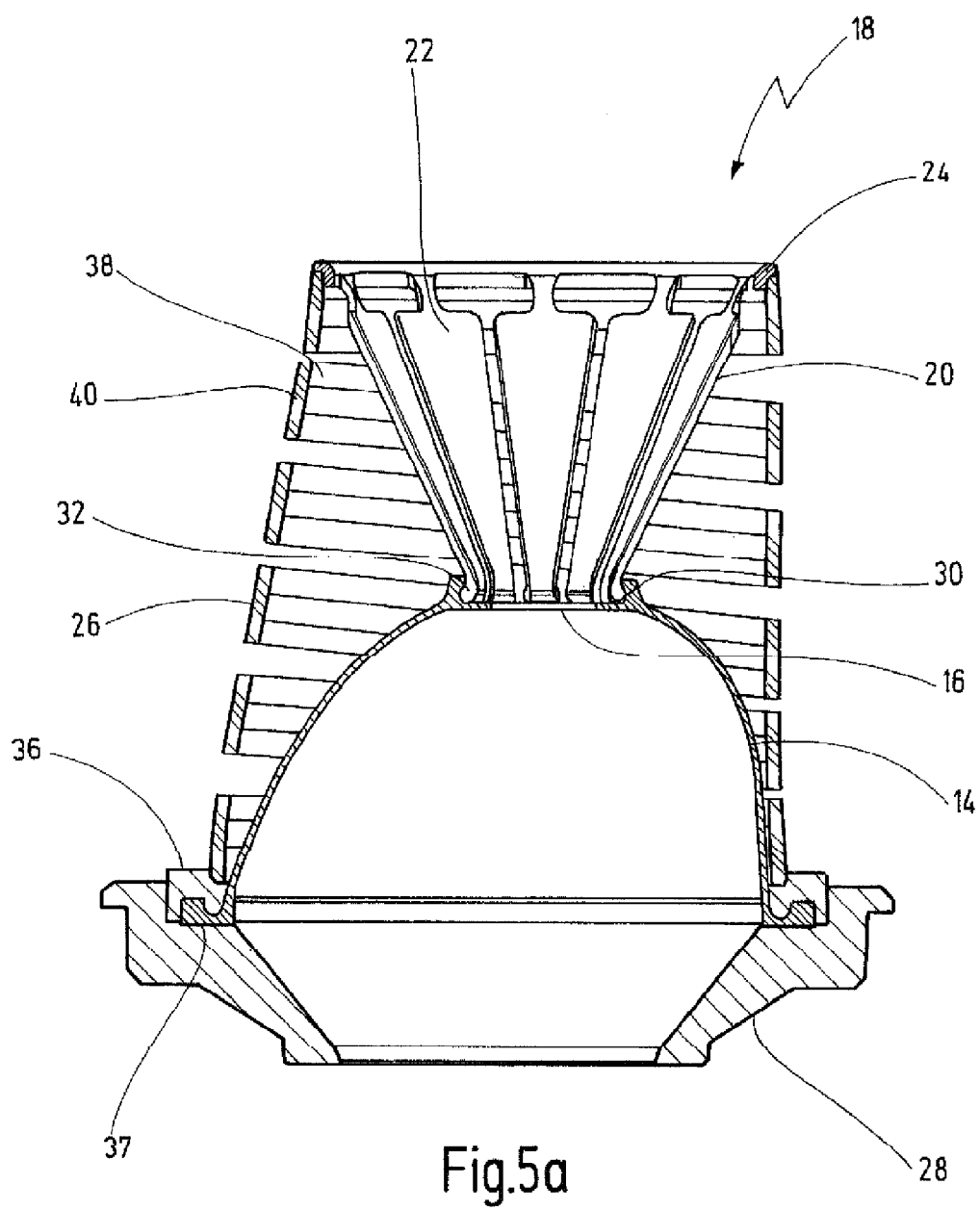
FIG. 5a shows the cross section after a lateral offset movement.

If a force is applied to the sealing system in the direction of the arrow 63, for example by the lateral offset of a shaft of smaller cross section, the expansion cone 20 moves along with the shaft in a movable flexible casing tube 26 of this kind (FIG. 5a). By means of the movement of the expansion cone 20 in the direction of the arrow 63, the proximal end of the casing tube 26 is similarly moved. The resulting offset between the proximal end and distal end of the casing tube 26 is compensated by the flexibility of the latter, such that it has a curved profile.

During such a movement of the expansion cone 20, the connection between the slats 22 and the socket 30 ensures a corresponding deformation of the seal 14. The result of this is that the shaft, despite the offset, has a central position in the opening 16 of the seal 14 and does not become wedged in the opening 16 and does not cause any loss of leaktightness. By means of the flexible casing tube 26, the sealing system thus adapts to any offset of a shaft in the medical instrument.

Figure 8:
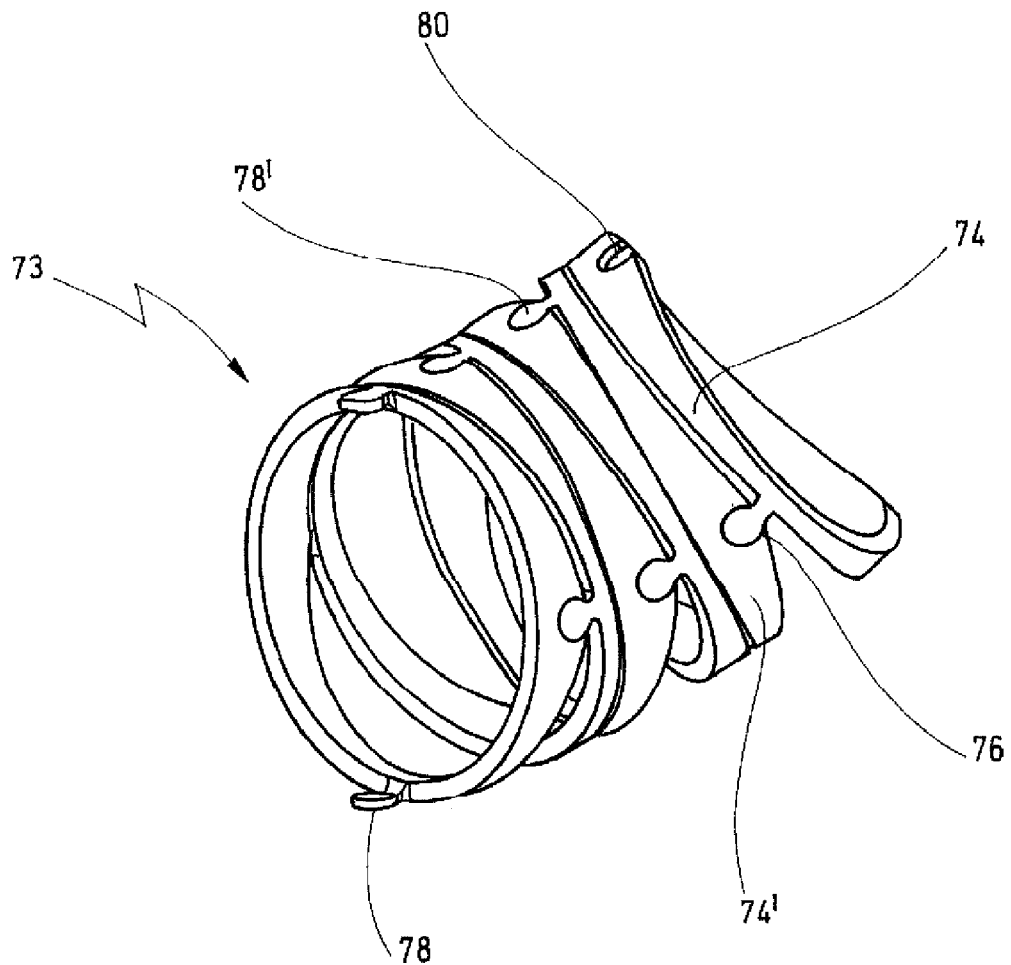
FIG. 8 shows a perspective view of a flexible casing tube with tilting joints.

A second embodiment of a flexible casing tube is shown in FIG. 8. In contrast to the casing tube 26 shown in FIG. 4, which can be produced as a single part by means of an injection moulding technique, for example, FIG. 8 shows a casing tube 73 composed of separate ring elements 74. These ring elements 74 have two different sides. Whereas one side has two tilting-joint sockets 80, the other side has two tilting-joint inserts 78 extending away from the ring body. The tilting-joint inserts 78 and the tilting-joint sockets 80 are arranged opposite each other. The tilting-joint socket 80 and the tilting-joint insert 78 on a ring element 74 are arranged in a circle and offset by 90° to each other.

As is shown in FIG. 8, several ring elements 74 are interconnected by connection of the tilting-joint inserts 78 of one ring to the tilting-joint sockets 80 of another ring. In this way, the casing tube 73 is formed which, with its connections between the tilting-joint inserts 78 and the tilting-joint sockets 80, resembles the webs 40 between the ring elements 38 of the casing tube 26 (FIG. 4 and FIG. 8). The tilting-joint insert 78 and the tilting-joint socket 80 thus form a tilting joint 76, which is responsible for the flexibility of the casing tube 73.

To obtain the greatest possible range of mobility, the height of a ring element 74 is higher at the tilting-joint sockets 80 than at the sites of the tilting-joint inserts 78 (FIG. 8). The ring element 74 can thus be pivoted further about the axis formed by the radially opposite tilting joints 76. A first ring element 74 can thus be pivoted, at the site of the tilting-joint socket 80, to a second ring element 74' further than if the latter at the site of the tilting-joint insert 78' were to have the same height as at the site of the tilting joint 76.

In this way, with this illustrative embodiment too, the same effect is achieved, upon a lateral offset of an inserted shaft, as has been explained for the flexible casing tube 26 in connection with FIG. 5 and FIG. 5a.

Figure 9:
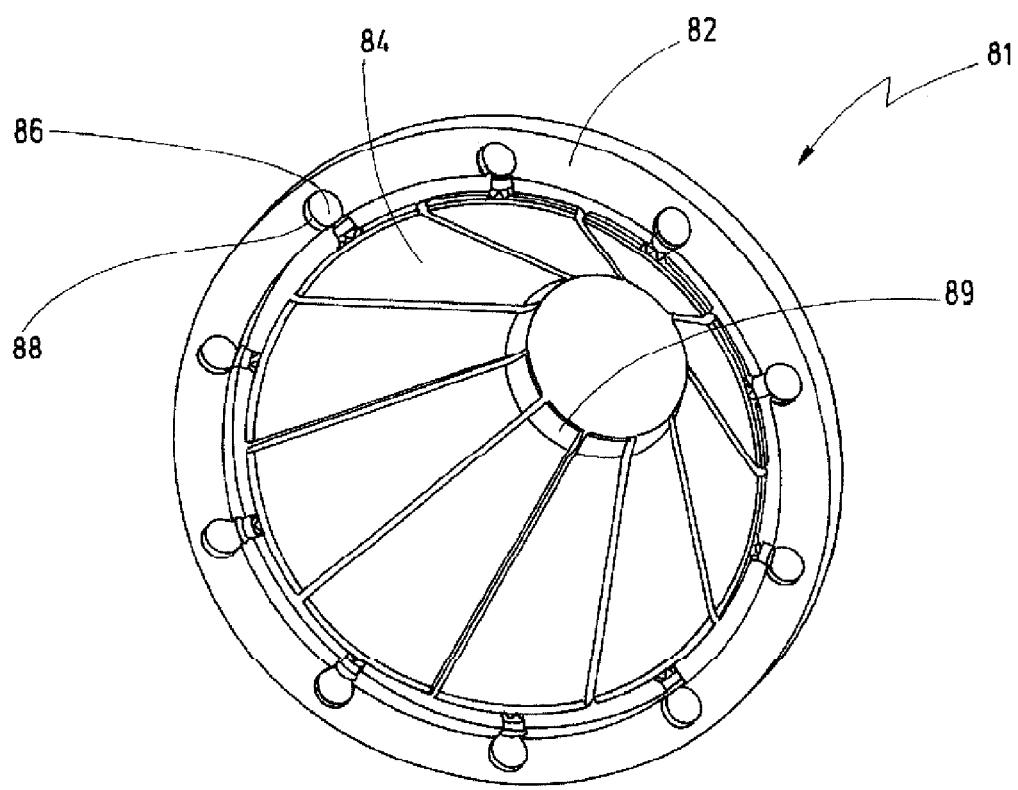
FIG. 9 shows a perspective view of an expansion cone with slats that comprise a spherical head.
Figure 10:
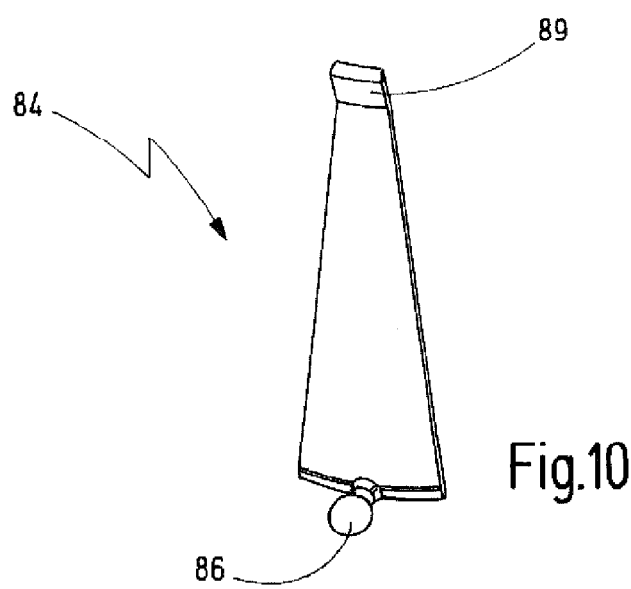
FIG. 10 shows a perspective view of an individual slat comprising a spherical head.

A second embodiment of slats is shown in FIGS. 9 and 10. A slat 84 shown there has an endpiece 89 at the distal end and a spherical head 86 at the proximal end.

This spherical head 86 serves for movable connection of the slat 84 to an annular body 82. For this purpose, the annular body 82 has corresponding openings 88 into which the spherical heads 86 can be inserted. It is conceivable for the slats to be inserted in the manner of a catch mechanism and also a simple engagement mechanism. For the latter alternative at least, a cover ring (not shown here) would also be required to prevent the slats 84 from falling out of the annular body 82 (FIG. 9).

In this way, an expansion cone 81 is obtained similar to the expansion cone 20 with the film hinges 34 in the previously mentioned illustrative embodiment. Similarly to the latter, the slats 84 also narrow from the proximal end to the distal end.

What is claimed is:

1. A medical instrument having
   a cannula
   a seal disposed in said cannula, said seal has an opening for guiding a shaft of another instrument through said seal and said cannula in a sealed manner,
   an expansion device for expanding said opening in said seal for guiding shafts of said other instruments of greater diameter in a sealed manner through said expanded opening, said expansion device having an expansion cone comprising a plurality of slats mounted pivotably on an annular body at a first end, a second end of said slats opposite to said first end, being connected to said seal in an area of said opening, and
   a flexible casing structure accommodating said seal and said expansion device; wherein said flexible casing structure is a flexible casing tube that is composed of a series of substantially parallel ring elements; and
   wherein said seal is designed as a pot-seal having said opening in a bottom of said pot, said pot-seal extending in a distal direction away from a distal end of said expansion cone.

2. The medical instrument of claim 1, wherein two adjacent ring elements of said series of ring elements are connected one to another at two radially opposite sites.

3. The medical instrument of claim 2, wherein said sites connecting a ring element to a distally adjacent ring element are in each case always offset by 900 with respect to connecting sites connecting a proximally adjacent ring element.

4. The medical instrument of claim 2, wherein the connection at said connection sites are flexible webs.

5. The medical instrument of claim 2, wherein a connection at said connection sites are tilting joints.

6. The medical instrument of claim 5, wherein a ring element has at least one tilting joint socket and at least one tilting-joint insert extending radially from said ring element, a height of a ring element being higher at a site of a tilting-joint socket than at a site of a projecting tilting-joint insert.

7. The medical instrument of claim 1, wherein said flexible casing structure widens conically from a proximal end to a distal end thereof.

8. The medical instrument of claim 1, wherein said second end of said slats of said expansion cones are connected with a form fit to a socket at an edge of said opening in said seal.

9. The medical instrument of claim 1, wherein said second end of said slats of said expansion cone are adhesively bonded to said seal.

10. The medical instrument of claim 1, wherein said expansion cone is composed of eight to twelve slats.

11. The medical instrument of claim 1, wherein said expansion cone is composed of ten slats.

12. The medical instrument of claim 1, wherein said expansion cone is made of a hard plastic.

13. The medical instrument of claim 1, wherein said flexible casing structure is made of a hard plastic.

14. The medical instrument of claim 1, wherein said seal is made of an elastic material.

* * * * *